United States Patent [19]

Cheetham

[11] 4,427,628
[45] Jan. 24, 1984

[54] DENTAL AMALGAM ALLOY

[76] Inventor: Jeffery J. Cheetham, 5 Brunsdon St., Bayswater, Victoria, Australia, 3153

[21] Appl. No.: 312,777

[22] Filed: Oct. 19, 1981

[30] Foreign Application Priority Data

Nov. 28, 1980 [AU] Australia .............................. PE6679

[51] Int. Cl.$^3$ ........................ C22C 5/06; C22C 30/02; C22C 30/04; C22C 30/06
[52] U.S. Cl. .................................. 420/504; 420/502; 420/580; 420/587; 420/589
[58] Field of Search ............. 75/0.5 B, 134 B, 134 C, 75/173 C, 251, 255; 433/207, 222; 420/502, 504, 580, 587, 589

[56] References Cited

U.S. PATENT DOCUMENTS

| | | | |
|---|---|---|---|
| 2,024,545 | 12/1935 | Stack | 75/173 C |
| 3,997,330 | 12/1976 | Aliotta et al. | 75/0.5 R |
| 4,030,918 | 6/1977 | Sung et al. | 75/134 B |
| 4,255,192 | 3/1981 | Burns | 75/134 C X |

*Primary Examiner*—Brian E. Hearn
*Assistant Examiner*—David A. Hey
*Attorney, Agent, or Firm*—William R. Hinds

[57] ABSTRACT

The present invention relates to low in silver particulate dental amalgam alloys comprising by weight from about 46 to 48% silver, about 23 to 33% tin, about 20 to 28% copper and about 0.5 to 5% indium.

The dental amalgam alloys of the present invention have been found to be particularly efficacious when incorporated in blends with high silver particulate dental amalgam alloys, said high silver alloys being used in amounts between about 30% and 70% of the total alloy blend.

7 Claims, No Drawings

DENTAL AMALGAM ALLOY

The present invention relates to dental amalgam alloys. Dental alloys are typically silver based alloys which can be admixed in particulate form with mercury to produce an amalgam which is initially soft and pliable but which sets to a hard mass after a time. Thus, when fresh amalgam is placed in a tooth cavity it can be worked by the dentist to completely fill the cavity and to have an external configuration consistent with that of the remainder of the tooth.

Conventionally, silver based dental alloys contain a major proportion of silver such as from 65 to 75% by weight. The balance may be made up of a number of elements but is usually made up chiefly with tin and copper.

However, the prices of silver has increased dramatically in recent times and all the indications are that the price of silver will remain high for the foreseeable future.

Therefore the present invention provides a dental alloy which comprises a lower proportion of silver than has been used conventionally. The alloy of the present invention also has desirable properties for dental purposes including good compressive strength, dimensional change and static creep properties.

In accordance with the present invention there is provided a dental amalgam alloy comprising by weight from about 41 to 48% silver, about 23 to 33% tin, about 20 to 28% copper and about 0.5 to 4% indium.

Preferably the alloy of the present invention comprises by weight from about 44 to 48% silver, about 27 to 30% tin, about 22 to 26% copper and about 1 to 4% indium.

More preferably, the alloy of the present invention comprises by weight from about 45 to 47% silver, from about 27 to 29% tin, from about 23 to 25% copper and from about 1 to 3% indium. The alloy is used in the form of discrete particles which are preferably spherical since the formation of spherical particles tends to produce an alloy which in the resultant amalgam leads to a low Gamma 2 content. Gamma 2 content is desirably kept low since this component of an amalgam is the weakest and most corrodible component thereof.

Preferably, a spherical alloy composition of the present invention is produced by the method described and claimed in co-pending Australian Patent Application No. 58104/80 and U.S. patent application Ser. No. 062,343, now U.S. Pat. No. 4,264,354. Basically, this method usually involves forming conventional lathe cut chip particles of the alloy, entraining the so formed chip particles in a stream of an inert carrier gas under pressure, passing the stream of inert carrier gas containing the particles through a heating zone so as to melt at least a surface stratum of the particles and then cooling the particles so as to solidify the melted portions of the particles.

The process is preferably conducted in a closed container containing an atmosphere of inert gas such as nitrogen or air. The inert carrier gas may be nitrogen or compressed air. Preferably, the inert carrier gas has a pressure in the range from 40 to 100 p.s.i., more preferably in the range from 45 to 55 p.s.i. Conveniently, the particles may be cooled by being immersed in a liquid which may be water.

Preferably, the heating zone is in the form of a flame having a reducing flame section in the form of a cone surrounded by an oxidising section, and the particles are passed through the reducing section. The flame may be produced by combustion of oxy-acetylene, hydrogen or liquid petroleum gas.

As an alternative to the flame, the heating zone may be in the form of a heated region produced by a high frequency induction coil.

Previously known spherical dental alloys usually result in a dental amalgam that has a negative dimensional change. That is, during the setting procedure in the tooth cavity, the amalgam actually contracts. This results in secondary caries being created between the amalgam and the tooth. This is known as marginal leakage.

It is now found, that by using spherical dental amalgam alloys according to the present invention which have been produced by the method of Australian Patent Application No. 58104/80, (U.S. application Ser. No. 062,343, now U.S. Pat. No. 4,264,354) that in many cases the resulting amalgam actually tends to expand on setting and thus fill the tooth cavity more closely than prior art spherical alloys. It is also found, that the spherical alloys produced by this method have good corrosion resistance.

The dental amalgam alloy of the present invention has been found to be particularly efficacious when incorporated in blends with particulate high-silver amalgam alloys although its properties when unblended are quite satisfactory for dental purposes. The high-silver amalgam alloy contains more than 50% by weight silver and is used in amounts between about 30% and 70% by weight of the total alloy blend, more preferably between about 35 and 55% by weight of the total alloy blend.

Preferably, this high-silver alloy contains by weight from about 60 to 80% silver, from about 1 to 6% copper, from about 23 to 33% tin and from 0 to about 3% zinc, more preferably from about 65 to 75% silver, from about 2 to 5% copper, from about 24 to 29% tin and from 0 to about 2% zinc. The further high-silver alloy in this blend may be formed of spherical particles or lathe cut particles.

Spherical dental amalgam alloys have a disadvantage in that they are often too mobile in the tooth cavity when being condensed by the dentist. The use of a blend of spherical particles in accordance with the present invention alleviates much of this problem.

Further, the use of the low silver amalgam alloy of this present invention in a blend of spherical particles results in amalgam of good strength, low static creep and controlled Gamma 2 phase.

Still further, a blend of spherical particles in accordance with the present invention results in amalgam which have excellent 30 minute compressive strength. This is very important since most amalgam filling failures are due to patient abuse in the first 30 minutes after placement of the amalgam. Compressive strength at 1 hour and at 24 hours are found to be comparable to those obtained with other known spherical alloys.

In another embodiment of this present invention, the low silver amalgam alloy of the present invention is blended with a lathe cut chip alloy. The use of a proportion of lathe cut chip alloy has the advantage that it gives the dentist more resistance when he is condensing amalgam into a tooth cavity. Once again, the use of the low silver amalgam alloy of the present invention in the blend results in amalgam alloys of good strength, low static creep and controlled Gamma 2 phase. Further, all of this particles present in the blend act to reduce Gamma 2 content in the resultant amalgam.

The amalgams produced by this blend also have excellent 30 minute compressive strengths.

Further, the all spherical and the sperical-lathe cut blends using the alloy of the present invention have a snap set. That is, there is a good working time of several minutes such as about four to five minutes after the formation of an amalgam before substantial setting takes place. Immediately after this period the setting reaction commences at a high rate. Other dental alloys tend to produce amalgam with a gradual setting curve commencing straight after formation of the amalgam.

The present invention will now be illustrated by the following examples.

In the following examples all amalgams were produced by admixing one part of weight of the alloy composition with one part by weight of mercury. The trituration time was 10 seconds in a vibrating mixer operating at a rate of 4,000 cycles per minutes.

A standard test specimen according to the American Dental Association Testing Method was prepared and the physical properties determined.

All the spherical alloys used were prepared in accordance with the method of Australian Patent Application No. 58104/80 (U.S. application Ser. No. 062,343, now U.S. Pat. 4,264,354). In each case, nitrogen at 50 p.s.i. was used as the carrier gas and the particles having size range distribution of 5-40 microns were injected, in an atmosphere of nitrogen, through the reducing cone of a flame produced by combusting liquid petroleum gas at 40 p.s.i. in air. The heat treated particles were passed into cooling water held at 5° C. The particles were subsequently retrieved from the water and cleaned with 2N hydrochloric acid and then vacuum dried at 60° C., and humidity stress relief annealed at 150° C. under reducing conditions.

EXAMPLE 1

A spherical dental amalgam alloy was produced as described above by the method of Australian Patent Application No. 58104/80 and had the following composition by weight:

| Silver | 46% |
| Tin | 28% |
| Copper | 24% |
| Indium | 2% |

The alloy admixed with mercury as described above formed an amalgam with the following properties:

| Compressive strength (PSI) | |
| --- | --- |
| 30 minutes | 23,000 |
| 1 hour | 33,000 |
| dimensional change | +5.7 micron/mm |
| Static creep % | 0.09 |

EXAMPLE 2

An alloy with the following composition by weight was prepared by the procedure of Example 1:

| Silver | 48% |
| Tin | 28% |
| Copper | 22% |
| Indium | 2% |

An amalgam prepared from this alloy by the procedure of Example 1 had the following properties:

| Compressive strength (PSI) | |
| --- | --- |
| 30 minutes | 20,000 |
| 1 hour | 30,000 |
| dimensional change | +3.1 micron/mm |
| Static creep % | 0.19 |

EXAMPLE 3

An alloy with the following composition by weight was prepared by the procedure of Example 1:

| Silver | 44% |
| Tin | 28% |
| Copper | 26% |
| Indium | 2% |

An amalgam prepared from this alloy by the procedure of Example 1 had the following properties:

| Compressive strength (PSI) | |
| --- | --- |
| 30 minutes | 18,000 |
| 1 hour | 28,000 |
| dimensional change | +3.0 micron/mm |
| Static creep % | 0.21 |

EXAMPLE 4

An alloy with the following composition by weight was prepared by the procedure of Example 1:

| Silver | 46% |
| Tin | 30% |
| Copper | 22% |
| Indium | 2% |

An amalgam prepared from this alloy by the procedure of Example 1 had the following properties:

| Compressive strength (PSI) | |
| --- | --- |
| 30 minutes | 18,000 |
| 1 hour | 28,000 |
| dimensional change | −0.9 micron/mm |
| Static creep % | 0.19 |

EXAMPLE 5

An alloy with the following composition by weight was prepared by the procedure of Example 1:

| Silver | 46% |
| Tin | 28% |
| Copper | 25% |
| Indium | 1% |

An amalgam prepared from this alloy by the procedure of Example 1 had the following properties:

| Compressive strength (PSI) | |
| --- | --- |
| 30 minutes | 20,000 |
| 1 hour | 29,000 |
| dimensional change | +0.7 microns/mm |
| Static creep % | 0.10 |

EXAMPLE 6

An alloy with the following composition by weight was prepared by the procedure of Example 1:

| | |
| --- | --- |
| Silver | 46% |
| Tin | 27% |
| Copper | 23% |
| Indium | 4% |

An amalgam prepared from this alloy by the procedure of Example 1 had the following properties:

| Compressive strength (PSI) | |
| --- | --- |
| 30 minutes | 20,000 |
| 1 hour | 30,000 |
| dimensional change | +3.3 micron/mm |
| Static creep % | 0.11 |

EXAMPLE 7

An alloy blend was prepared. This blend consisted of spherical particles and 60% by weight of the blend was formed of the alloy of Example 1.

The balance of 40% by weight was formed of an alloy of the following composition by weight:

| | |
| --- | --- |
| Silver | 70% |
| Copper | 3.5% |
| Tin | 26% |
| Zinc | 0.5% |

This spherical alloy as produced as described above by the method of Australian Patent Application No. 58104/80. The alloy blend of this example was admixed with mercury as in Example 1. The resulting amalgam had the following properties:

| Setting time | 4 minutes 30 seconds |
| --- | --- |
| dimensional change | +.15 microns/mm |
| Static creep % | .2 |
| Compressive strength (PSI) | |
| 30 minutes | 20,000 |
| 1 hour | 33,000 |
| 2 hours | 68,000 |

EXAMPLE 8

An alloy blend was prepared. This blend consisted of a mixture of spherical articles and lathe cut chip particles. 50% by weight of the blend was formed of the alloy of Example 1. The balance of 50% by weight was formed of a lathe cut chip alloy of the following composition by weight:

| | |
| --- | --- |
| Silver | 67% |
| Tin | 27% |
| Copper | 4% |
| Zinc | 2% |

The alloy blend of this example was admixed with mercury as in Example 1. The resultant amalgam had the following properties:

| Setting time | 4 minutes 30 seconds |
| --- | --- |
| dimensional change | +.10 microns/mm |
| Flow % | .12 |
| Static creep % | .7 |
| Compressive strength (PSI) | |
| 30 minutes | 18,000 |
| 1 hour | 28,000 |
| 2 hours | 65,000 |

Modifications and variations such as would be apparent to a skilled addressee are deemed within the scope of the present invention.

I claim:

1. A dental amalgam alloy which is a blend of high-silver particulate dental amalgam alloy consisting essentially by weight of about 60 to 80% silver, about 1 to 6% copper, about 23 to 33% tin and 0 to about 3% zinc, and a spherical low-silver particulate dental amalgam alloy consisting essentially by weight of about 41 to 48% silver, about 23 to 33% tin, about 20 to 28% copper and about 0.5 to 4% indium, said high-silver alloy being present in an amount from about 30 to 70% by weight of the total alloy blend, and said low-silver alloy having been rendered spherical by entraining solid chip particles in a stream of an inert carrrier gas under pressure, passing the stream of inert carrier gas containing the particles through a heating zone so as to melt at least a surface stratum of the particles and then cooling the particles so as to solidify the melted portions of the particles.

2. A dental amalgam alloy blend according to claim 1, in which said high-silver alloy consists essentially by weight of about 65 to 75% silver, about 2 to 5% copper, about 24 to 29% tin and 0 to about 2% zinc.

3. A dental amalgam alloy blend according to claim 1, in which said high-silver alloy is in the form of spherical particles.

4. A dental amalgam alloy blend according to claim 1, in which said high-silver alloy is in the form of chip particles.

5. A dental amalgam alloy blend ccording to claim 1, in which said high-silver alloy is present in an amount from about 35 to 55% by weight of the total alloy blend.

6. A dental amalgam alloy blend according to claim 1, in which said low-silver dental amalgam alloy consists essentially by weight of about 44 to 48% silver, about 27 to 30% tin, about 22 to 26% copper and about 1 to 4% indium.

7. A dental amalgam alloy blend according to claim 1, in which said low-silver dental amalgam alloy consists essentially by weight of about 45 to 47% silver, about 27 to 29% tin, about 23 to 25% copper and about 1 to 3% indium.

* * * * *